United States Patent [19]

Marble

[11] Patent Number: 5,095,894
[45] Date of Patent: Mar. 17, 1992

[54] UPPER EXTREMITY STABILIZER

[75] Inventor: Alan F. Marble, Billings, Mont.

[73] Assignee: Level-One Products, Inc., Billings, Mont.

[21] Appl. No.: 628,640

[22] Filed: Dec. 14, 1990

[51] Int. Cl.[5] .............................................. A61F 5/04
[52] U.S. Cl. ................................. 602/20; 128/878;
128/DIG. 15; 602/4; 602/62
[58] Field of Search ................... 128/83, 85, 87 R, 94,
128/171, 159, 869, 874, 877, 878, DIG. 15, 77;
2/44, 45

[56] References Cited

U.S. PATENT DOCUMENTS

| | | | |
|---|---|---|---|
| 530,038 | 11/1894 | Gallegos | 128/78 |
| 634,429 | 10/1894 | Comly | 2/45 |
| 1,129,515 | 2/1915 | Perry | 128/78 |
| 1,293,089 | 2/1919 | Hardy | 128/78 |
| 3,780,729 | 12/1973 | Garnett | 128/94 |
| 3,875,935 | 4/1975 | Drew | 128/87 R |
| 4,099,524 | 7/1978 | Cueman et al. | 128/DIG. 15 X |
| 4,198,964 | 4/1980 | Honneffer | 128/87 R |
| 4,302,849 | 12/1981 | Margetson | 2/44 |
| 4,378,009 | 3/1983 | Rowly | 128/83 |
| 4,550,724 | 11/1985 | Berrehail | 128/874 |
| 4,593,778 | 6/1986 | Miller | 128/3 |
| 4,628,913 | 12/1986 | Lerman | 128/78 |
| 4,644,939 | 2/1987 | Coleman | 128/78 |
| 4,785,803 | 11/1988 | Benckhuljsen | 128/87 R |
| 4,836,195 | 6/1989 | Berrehail | 128/83 |
| 4,878,490 | 11/1989 | Scott | 128/94 X |
| 4,910,818 | 3/1990 | Grabill et al. | 5/433 |
| 4,982,447 | 1/1991 | Henson | 2/44 X |
| 5,016,650 | 5/1991 | Marlar | 128/869 X |

FOREIGN PATENT DOCUMENTS

| | | | |
|---|---|---|---|
| 2612772 | 9/1988 | France | 128/87 R |
| 218952 | 5/1987 | United Kingdom | 128/87 R |

Primary Examiner—Robert Bahr
Assistant Examiner—L. Thomas

[57] ABSTRACT

An improved orthopedic upper extremity stabilizing device (20) applied as a positioning aid for supporting, restraining and/or immobilizing the limbs or joints of a human's upper extremity by means of a lightweight, formable, enveloping torso-covering device (22) with extremity stabilizing devices (26) that restrict movement during pre-hospital emergency care and transport, definitive care, medical procedures, and/or the recuperation and natural healing periods. The torso-covering device (22) and extremity stabilizing devices (26) are each of single assemblage comprised of one-quarter inch thick open-cell foam flame laminated to engageable-loop material. The torso-covering device is closed with detachable engageable-hook closure straps (24). The extremity stabilizing devices (26) are applied to the torso-covering device by engageable-hook tape strips that are attached to the longitudinal edges of one planter surface of each device. The polymer-coated aluminum stays (28) are applied to stiffen extremity stabilizing devices when medically indicated, and are comprised of aluminum strips coated with polyvinyl chloride plastic with pressure sensitive engageable-hook adhesive tape is attached to a plan surface.

7 Claims, 4 Drawing Sheets 5,095,894

UPPER EXTREMITY STABILIZER

FIELD OF INVENTION

This invention relates to an improved orthopedic stabilizing device used to immobilize body limbs or joints, which is primarily concerned with immobilization of a human's upper extremity by using a lightweight, formable, enveloping torso vest with extremity binders.

BACKGROUND OF THE INVENTION

The present invention provides a new and improved orthopedic upper extremity stabilizing device that is used as a positioning aid for supporting, restraining and/or immobilizing the upper extremity limbs or joints of a human's upper extremity by using a lightweight, formable, enveloping torso vest with extremity binders that restrict a patient's freedom of movement during pre-hospital emergency care and transport, during full medical procedures, or during the recuperation and natural healing periods. Accordingly, this invention increases the stability and immobilizes the upper extremity by ensuring prevention of unwanted patient skeletal movements which generally complicate the natural healing processes.

Heretofore, methods and devices for stabilizing and immobilizing upper extremity limbs and joints consisted of adaptations form the traditional orthopedic sling and swathe devices used when moving injured people from an accident site to a location where bone fractures and dislocations could be reduced and cast. The sling is a device which supports the upper extremity from the elbow to the wrist using the neck as a means of attachment and support. The swathe is a device that binds the upper extremity between the shoulder and the elbow against the torso when applied circumferential around the torso as a means of attachment and support. Together, the sling and swathe devices are rather primitive state-of-the-art treatment for certain upper extremity injuries that require stabilization and/or immobilization during the natural healing and recuperative periods, especially wherever casting of fractures is often difficult, impossible, or contraindicated. The sling and swathe devices do not take advantage of the newer materials that allow safer stabilization and better immobilization with fewer disadvantages.

The principle disadvantage of the aforementioned prior art is that when the swathe device is applied appropriately to prevent upper extremity skeletal movement, it is both physically and psychologically distressful to the patient. The torso is compressed by the circumferential swathe device in order to stabilize and/or immobilize the upper extremity against the torso. This can result in patient respiratory embarrassment and/or ischaemic tissue development under the swathe device. Contrarily, if the swathe device is applied too loosely in an attempt to correct the above stated disadvantage, the device can easily slip upward, coming off over the shoulder during periods of activity or sleep. A loose swathe device may also allow the injured upper extremity to move independently of the torso during body movement, thereby defeating its stabilization and/or immobilization purpose. This results in unnecessary patient pain, discomfort, and unwanted skeletal rotational movement of the humerus and forearm bones which generally complicate the natural healing processes.

Further disadvantages occur when both the swathe and sling devices are used in combination. Neither the sling nor the swathe devices are easily or accurately adjusted; both devices require multiple adjustments in order to achieve the desired stabilization and/or immobilization results, thereby creating unnecessary patient manipulation during the application process. The sling device is inherently uncomfortable on patients as a result of the entire upper extremity weight being support by the device and thereby transferred to the neck soft tissues and muscles where the sling device narrows and ties as a means of attachment, causing premature patient fatigue, unnatural posturing, sore muscles, skin contusions, ischaemia and abrasions, and general patient irritability.

Coleman, U.S. Pat. No. 4,644,939 discloses a vest-like device that the wearer applies by inserting each arm into respective sleeve portions. Adjustments of the horizontal and diagonal elastic webbing that is anchored to this vest-like device provides tension to force and guide the humerus upward along its longitudinal axis into the glenoid fossa. Coleman recommends supporting the forearm with a wrist cuff during the early treatment of the shoulder injury. The disadvantage of this type of device is that it is designed for a dislocated shoulder type injury which stabilizes the shoulder joint only, allowing the upper extremity to move independent of the torso during limited body movement, thereby reversing the immobilization characteristics necessary to prevent unwanted skeletal rotational movement of the upper extremity during long bone fractures.

In one aspect, these orthopedic brace and support inventions disclosed generally feature a vest-like construction: U.S Pat. No 530,038, Gallegos; U.S. Pat. No. 634,429, Comly; U.S. Pat. No. 4,302,849, Margetson; U.S. Pat. No. 4,593,788, Miller. In addition, these inventions also feature stretchable or resilient type fabric construction, U.S. Pat. No. 1,129,515, Perry and U.S. Pat. No. 1,293,089, Hardy.

SUMMARY OF THE INVENTION

This instant invention succeeds the above-stated disadvantages in prior art by providing a new and improved orthopedic upper extremity stabilizing device which snugly follows the upper extremity body contours affording patient comfort and safety during the quick and easy application of the torso-covering and upper extremity stabilization portions. These portions effectively secure the upper extremity to the torso resulting in a positive immobilization of the joint above, the joint below, and the injured area, thereby adhering to traditional age-old orthopedic immobilization principles, while providing a greater degree of positive immobilization and selective patient extremity positioning than the sling and swathe type devices effectively provide.

An important object of this orthopedic upper extremity stabilizing device is to provide an effective means to: eliminate rotational movement of the humerus by providing positive immobilization of the forearm against the torso; provide easily adjusted variable positioning of the upper extremity against the patient's torso without any loss of immobilization; redistribute unnecessary weight and strain from the neck and spinal column to the shoulders; mitigate sore muscles, body fatigue and unnatural posturing, by replacing excessively constrictive binding with more natural movement restricting devices.

Another object is to provide an orthopedic upper extremity stabilizing device which is constructed of an ultra-light, formable, breathable, open-cell soft-good type material which allows for ease of patient motion and comfort without embarrassing any respiratory efforts, or impeding normal capillary circulation, while affording near normal skin regulation by allowing air to circulate throughout the enclosed body portions.

Still another object is to provide an orthopedic upper extremity stabilizing device that is of one piece construction with reversible application, allowing the device to be used bilaterally to stabilize the patient's upper extremity on either the right or left side.

A further object is to provide an orthopedic upper extremity stabilizing device that is economical to use, produce, and may be reused or disposed of after use, and further can be custom fit to each medical patient by a physician or paramedical personnel with only the use of a pair of scissors.

Still another object is to provide an orthopedic upper extremity stabilizing device that prevents inadvertent movement or slipping during physical exertion or sleep periods. Such device also readily allows the use of elbow traction weights. Patient comfort is an important object of this device which permits anatomic positional changes, eliminates pressure and discomfort points, skin chafing and irritation, and keeps the patient comfortable while providing improved immobilization.

Another object is to provide a simple orthopedic upper extremity stabilizing device that is less obvious and objectionable in appearance, that can be applied as environmental conditions require, over or under patient's clothing, further allowing for the safe removal and reliable re-application in a non-medical atmosphere to afford personal hygiene measures and device cleaning.

Among the objects of this instant invention are provisions for an improved orthopedic upper extremity stabilizing device which overcomes the above discussed disadvantages or undesirable features of the prior art, as well as others not mentioned. Accordingly, the reader shall see that the torso-covering device of this invention, FIG. V can be: manufactured as one piece; as two pieces sewn together on one lateral side; as two pieces sewn together at the shoulder loops; as two pieces with the lateral sides and top shoulder loops left open, using engageable-hook closure straps as a means of closure and adjustment of the lateral sides and/or elongated shoulder portions that are open with the above processes; manufactured with engageable-loop material on one planter surface only, with the engageable-hook closure straps attached permanently on the torso-covering device, which therefore, creates a need for left and right sided upper extremity stabilizers; manufactured without engageable-loop material, substituting any fabric material for engageable-loop tape, allowing limited extremity adjustment according to placement of loop tape on torso-covering device; manufactured with only one elongated shoulder portion, using any of the above processes of manufacturing, changes of material, and means of attachment.

The orthopedic upper extremity stabilizing device is a highly reliable, lightweight, yet economical orthopedic device which can be used by persons of almost any age. While the description contains many specificities, these should not be construed as limitations on the scope of the invention, but rather as an exemplification of one preferred embodiment thereof. Many other variations are possible. For example: to stabilize and/or immobilize torso ribs; provide a means of attachment for surgical, trauma, burn, or any other type of torso dressings; provide a means of attachment for hyperthermia or cryotherapy packs; used to provide passive torso restraint of wheel chair bound patients; used as children game where ping-pong type balls or other soft objects covered with engageable-hook tape are thrown at the wearer.

Further objects and advantages of the invention will be readily apparent from the reading of the following description of a device constructed in accordance with the invention, and reference to the accompanying drawings, wherein:

BRIEF DESCRIPTION OF THE DRAWINGS

The present invention is illustrated by way of example in the figures of the accompanying drawing in which.

Figure 1:
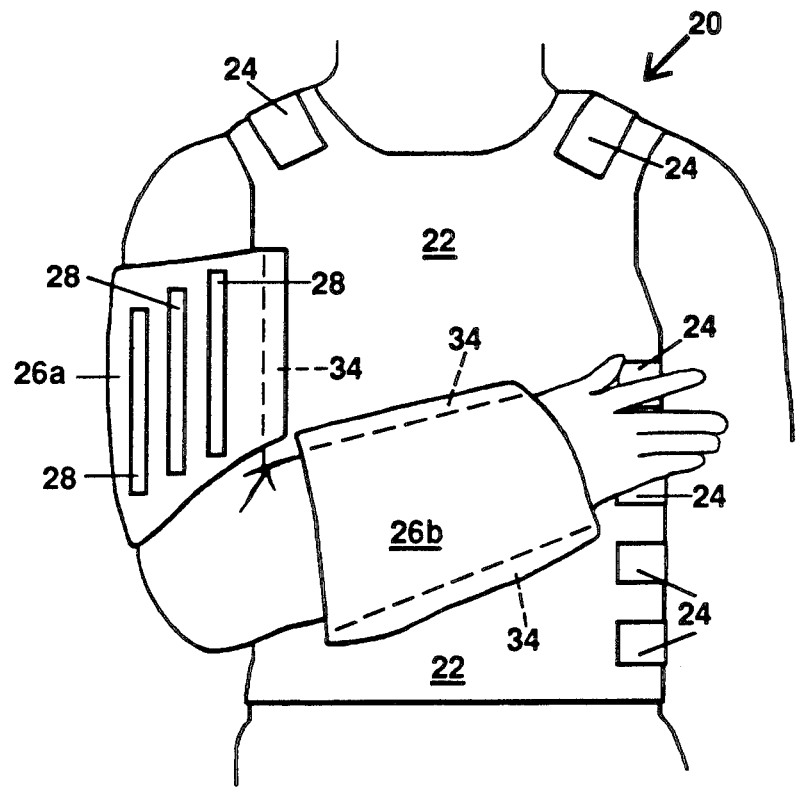
FIG. 1 illustrates a front view of the upper extremity stabilizer in accordance with the present invention.
Figure 2:
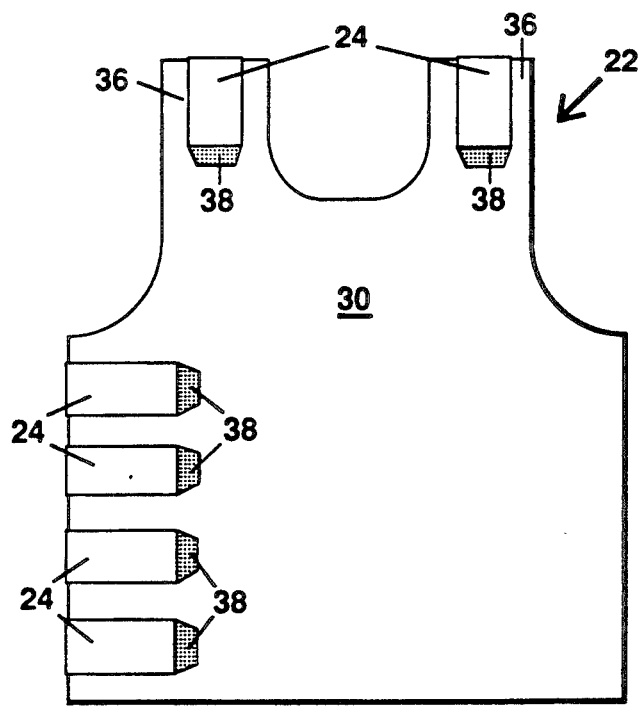
FIG. 2 illustrates a back view of the torso-covering device with the means of closure.
Figure 3:
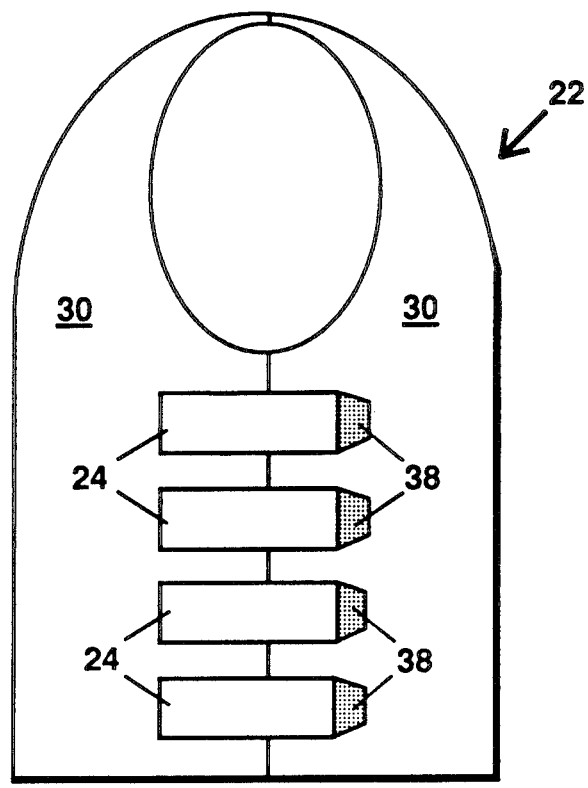
FIG. 3 illustrates a side elevation view of the means of closure.
Figure 4:
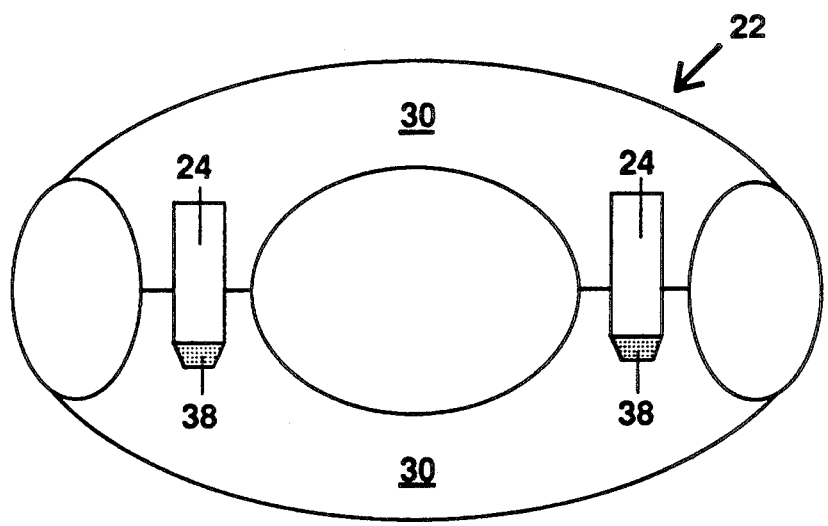
FIG. 4 illustrates a top plan view of the means of closure.
Figure 5:
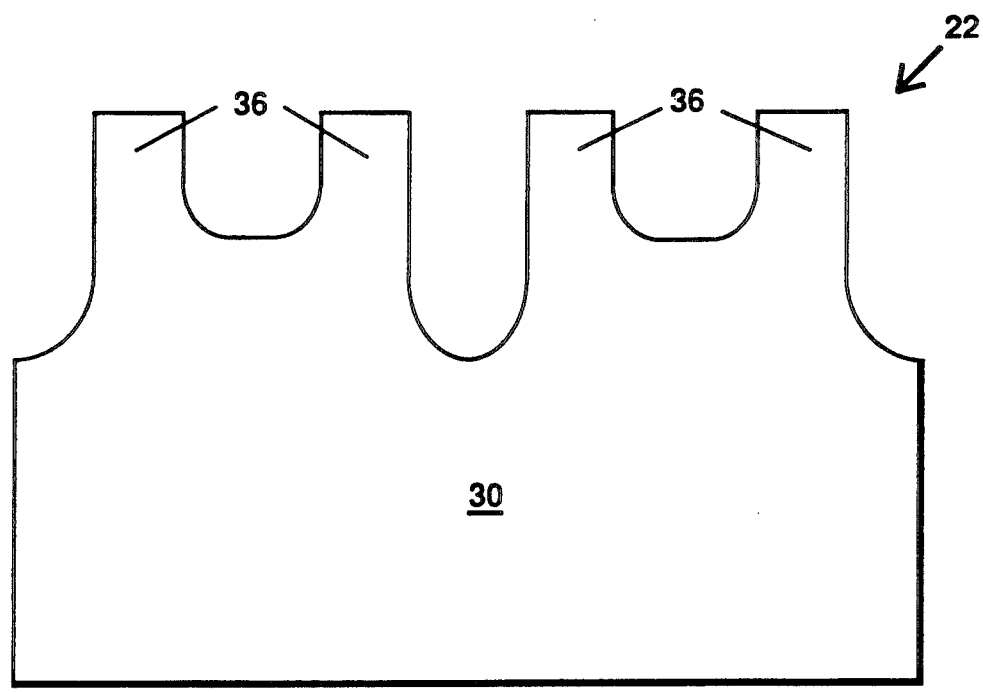
FIG. 5 illustrates a plan view of the torso-covering device.
Figure 6:
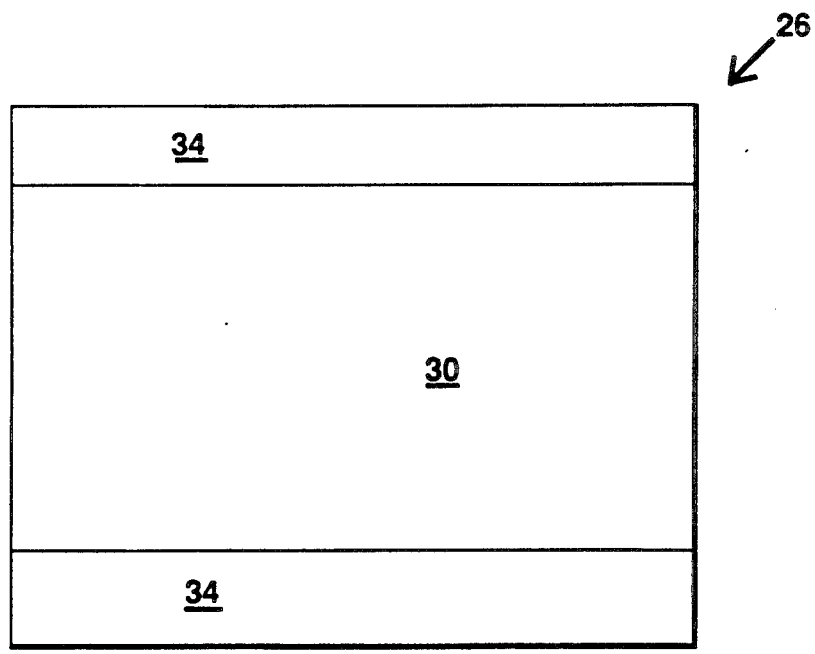
FIG. 6 illustrates a top plan view of the extremity stabilizing device.
Figure 7:
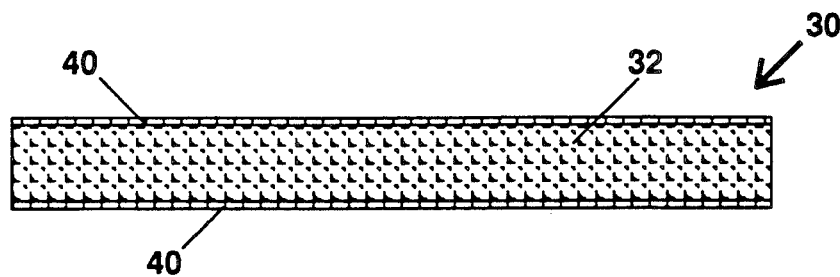
FIG. 7 illustrates a cross section view of the double-sided engageable-loop laminate.
Figure 8:
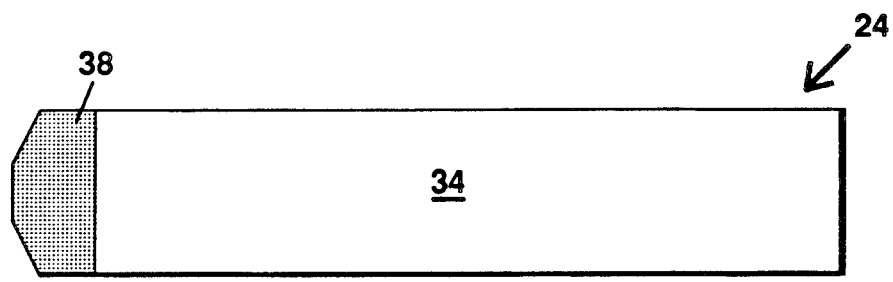
FIG. 8 illustrates a top plan view of the engageable-hook closure strap.
Figure 9:
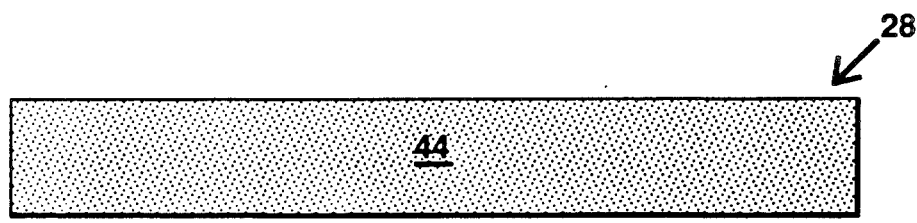
FIG. 9 illustrates a top plan view of the detachable polymer-coated aluminum stay.
Figure 10:
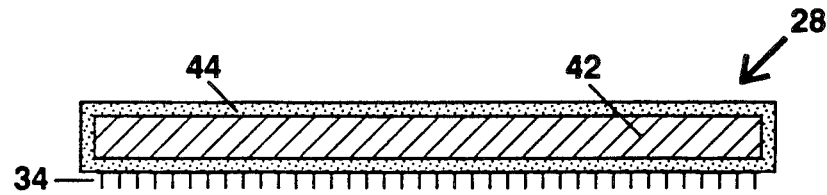
FIG. 10 illustrates a cross section view of the detachable polymer-coated aluminum stay.

Corresponding reference characters indicate corresponding parts throughout the several views of the drawings. The exemplifications set out and illustrate the preferred embodiments of the present invention in one form thereof, and such exemplifications are not to be construed as limiting either the scope of the disclosure thereof in any manner.

REFERENCE NUMERALS IN DRAWINGS

| | |
|---|---|
| 20 | upper extremity stabilizer |
| 22 | torso-covering device |
| 24 | engageable-hook closure straps |
| 26a | extremity stabilizing device |
| 26b | extremity stabilizing device |
| 28 | detachable polymer-coated aluminum stay |
| 30 | double-sided engageable-loop laminate |
| 32 | open-cell foam core |
| 34 | engageable-hook tape |
| 36 | elongated shoulder portions |
| 38 | removal tab |
| 40 | engageable-loop material |
| 42 | aluminum material |
| 44 | polymer coating |

DETAILED DESCRIPTION OF THE PREFERRED EMBODIMENTS

The upper extremity stabilizer 20 is comprised of a torso-covering device 22, six engageable-hook closure straps 24, two extremity stabilizing devices 26a and 26b, and six detachable polymer-coated aluminum stays 28.

The torso-covering device 22 is of a one piece unibody, sleeveless, vest-like construction with the anterior and posterior aspects of the torso-covering device 22 being of the same size and construction, as best shown in FIG. V. The torso-covering device 22 is comprised of a one-quarter of an inch thick open-cell foam core 32, having an engageable-loop material 40 flame laminated to the front and back plan surfaces, as best shown in FIG. VII. The posterior aspect of the torso-covering device 22, as best shown in FIG. II, extends midline from the waist of the wearer to slightly above the shoulder blades; with the anterior aspect extending midline from the waist of the wearer to slightly below the clavicular girdle, as best shown in FIG. I. The torso-covering device 22 envelopes the torso, starting from one lateral aspect, wrapping around the anterior torso to the opposite lateral aspect, then continuing around through the posterior aspect closing at the point of beginning with four engageable-hook closure straps 24, positioned evenly from just below the axilla to just above the waist of the wearer, as best shown in FIG. III. Two elongated shoulder portions 36 extend from the superior aspect of both the posterior and anterior portions of the torso-covering device 22, each closing with an engageable-hook closure strap 24, as best shown in FIG. IV.

The engageable-hook closure straps 24 are comprised of six engageable-hook tape strips of sufficient width 1" to 2" and length 4" to 6" to provide a secure means of closure; one end of the engageable-hook closure straps 24 are folded over approximately one-half inch and ultrasonically welded forming the removal tabs 38, as shown in detail in FIG. VIII.

The extremity stabilizing devices 26a and 26b are comprised of double-sided engageable-loop laminate 30 of sufficient width 6" to 8" and length 6" to 8" with two engageable-hook tape 34 strips of sufficient width ¾ to 1" and length 6" to 8" attached to one surface at opposite ends of each extremity stabilizing device 26a and 26b, as shown in detail in FIG. VI, to provide a secure means of attachment and provide adequate stabilization of the upper extremity to the torso-covering device 22.

The polymer-coated aluminum stay 28 is comprised of an aluminum strip, coated with a polyvinyl chloride plastic, as best shown in FIG. IX, that is of sufficient thickness 0.032" and width ½ and ¾ and length 6" and 8" to provide additional stiffening of extremity stabilizing devices 26a and 26b. Using one of the plan surfaces of the polymer-coated aluminum stay 28 is attached with pressure sensitive engageable-hook tape 34, as best shown in FIG. X, which provides the means of attachment to the extremity stabilizing devices 26a and 26b.

OPERATION OF INVENTION

In operation, the upper extremity stabilizer 20 is placed on the wearer by applying the torso-covering device 22 on the wearer starting from the injured side. The torso-covering device 22 is placed between the injured extremity and the torso, positioning the closed lateral side, under the axilla, then wrapping the anterior and posterior portions around the torso with the ends meeting or overlapping on the open lateral side, taking care to overlap any excess toward the back. Secure the torso-covering device 22 in place with four engageable-hook closure straps 24, positioned from just below the axilla to the waist of the wearer, with the removal tab 38 facing posterior. Secure the elongated shoulder portions 36 in place by bringing the posterior portions forward over the shoulder and overlap with the anterior portions to the rear, securing each elongated shoulder portion 36 with an engageable-hook closure strap 24 with the removal tab 38 facing the rear. Place the injured extremity against the torso-covering device 22, and apply the extremity stabilizing device 26a over the arm, securing the arm to the torso-covering device 22; then position the forearm and apply the extremity stabilizing device 26b over the forearm, securing the forearm to the torso-covering device 22. The polymer-coated aluminum stays 28 are now attached to the extremity stabilizing devices 26a and 26b, using the engageable-hook tape 34 means of attachment to provide additional long axis support when and where medically necessary.

I claim:

1. A medical device for stabilizing a human's upper extremity by using the torso as the primary supporting structure, comprising:
   a. a torso-covering device constructed of a lightweight, formable, torso enveloping material, with adjustable fitting and closure;
   b. a means for securing closure of the torso-covering device on the torso using removable closure straps;
   c. a means for securing the human's upper extremity to said torso-covering device using movable, position adjustable, extremity stabilizing devices, wherein said torso-covering device is constructed of double-sided engageable-loop material, thereby enabling said torso-covering device to be reversible, thereby permitting bilateral torso application.

2. The medical device in claim 1, wherein said torso-covering device is sleeveless, having a vest-like shape, with a uni-body flat construction.

3. The medical device of claim 1, wherein said torso-covering device can be easily cut with common scissors, thereby enabling a reduction in size, and custom alternation for atypical torsos.

4. The medical device of claim 1, wherein the means for securing closure consists of removable engageable-hook closure straps of sufficient length and width to provide secure closure and reversal of said torso-covering device.

5. The medical device of claim 1, wherein said means of attachment of said human's upper extremity to said torso-covering device consists of two extremity stabilizing devices of double-sided engageable-loop material with engageable-hook tape attached to the longitudinal edges of one planter surface of each extremity stabilizing device.

6. The medical device of claim 5, wherein said extremity stabilizing devices are of sufficient size to stabilize said human's upper extremity to the torso between the shoulder and elbow and between the elbow and hand.

7. The medical device of claim 5, wherein said extremity stabilizing devices include provision for the application of long axis, detachable polymer-coated aluminum stays.

* * * * *